(12) United States Patent
Penner

(10) Patent No.: US 10,492,490 B2
(45) Date of Patent: Dec. 3, 2019

(54) ADJUVANT COMPOSITIONS AND RELATED METHODS FOR REDUCING HERBICIDE VOLATILITY

(71) Applicant: BOARD OF TRUSTEES OF MICHIGAN STATE UNIVERSITY, East Lansing, MI (US)

(72) Inventor: Donald Penner, Williamston, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 2 days.

(21) Appl. No.: 15/058,500

(22) Filed: Mar. 2, 2016

(65) Prior Publication Data

US 2016/0255832 A1    Sep. 8, 2016

Related U.S. Application Data

(60) Provisional application No. 62/129,124, filed on Mar. 6, 2015.

(51) Int. Cl.
*A01N 25/32* (2006.01)
*A01N 25/02* (2006.01)

(52) U.S. Cl.
CPC ............. *A01N 25/32* (2013.01); *A01N 25/02* (2013.01)

(58) Field of Classification Search
None
See application file for complete search history.

(56) References Cited

U.S. PATENT DOCUMENTS

| | | | |
|---|---|---|---|
| 5,945,377 A | 8/1999 | Penner et al. | |
| 6,436,874 B1 * | 8/2002 | Kuah | A01N 57/20 504/128 |
| 6,617,280 B2 * | 9/2003 | Fafchamps | A01N 33/12 504/127 |
| 7,902,118 B2 | 3/2011 | Penner et al. | |

OTHER PUBLICATIONS 2,4-D Technical Fact Sheet, 11 pages, (Nov. 2008), accessed from http://nplc.orst.edu/factsheets/archive/2,4-DTech.html (retrieved on Mar. 2, 2016).
Reddy IT® Product Data Sheet, 2 pages (2011).

* cited by examiner

*Primary Examiner* — Alton N Pryor
(74) *Attorney, Agent, or Firm* — Marshall, Gerstein & Borun LLP

(57) ABSTRACT

The disclosure relates to adjuvant compositions and related methods for reducing herbicide volatility. The adjuvant- and herbicide-containing herbicide compositions are generally aqueous and include a volatile growth regulator herbicide and a monosaccharide adjuvant. When the compositions are applied to a target area to control a herbicide-sensitive target plant in the area with the herbicide, the monosaccharide adjuvant reduces volatile transport of the herbicide, thus reducing damage to other (non-target) sensitive plants, whether inside or outside of the target area of application.

22 Claims, No Drawings

ADJUVANT COMPOSITIONS AND RELATED METHODS FOR REDUCING HERBICIDE VOLATILITY

CROSS REFERENCE TO RELATED APPLICATION

Priority is claimed to U.S. Provisional Application No. 62/129,124 (filed Mar. 6, 2015), which is incorporated herein by reference in its entirety.

STATEMENT OF GOVERNMENT INTEREST

None.

BACKGROUND OF THE DISCLOSURE

Field of the Disclosure

The disclosure generally relates to adjuvant compositions and related methods for reducing herbicide volatility. The adjuvant- and herbicide-containing compositions generally include a volatile growth regulator herbicide and a monosaccharide adjuvant.

Brief Description of Related Technology

Volatilization of herbicides from soils and plants can result in undesirable loss of the active herbicide ingredient as well as unintended injury to nearby plants. Volatile growth regulator herbicides such as 2,4-D can cause damage to neighboring, herbicide-sensitive plants resulting from volatile transport of the herbicide within its intended target area and to other neighboring areas including the herbicide-sensitive plants.

Penner et al. U.S. Pat. No. 5,945,377 discloses compositions incorporating a non-volatile, post-emergence herbicide and a monosaccharide, particularly fructose, as a potentiator of the herbicide against weeds without decreasing tolerance of a crop plant to the herbicide. The compositions are used as a spray in water in a method for killing weeds.

SUMMARY

The disclosure relates to adjuvant compositions and related methods for reducing herbicide volatility. The adjuvant- and herbicide-containing compositions generally include a volatile growth regulator herbicide and a monosaccharide adjuvant. When the compositions are applied to a target area to control a target plant (e.g., a weed or other undesired plant) in the area with the herbicide, the monosaccharide adjuvant reduces volatile transport of the herbicide, thus reducing damage to other (non-target) sensitive plants, whether inside or outside of the target area of application. The compositions are suitably aqueous, and they can be in a relatively concentrated form (e.g., intended to be diluted with water, optionally with the addition of other additives or adjuvants prior to use) or in a relatively dilute form (e.g., at concentrations suitable for spraying or other application to a target area without dilution).

In one aspect, the disclosure relates to a method for reducing volatile transport of volatile herbicides, the method comprising: (a) providing a composition comprising: (i) water, (ii) a volatile growth regulator herbicide, and (iii) a monosaccharide, (b) applying the composition to a target area comprising: (i) optionally a first desired plant which is resistant or tolerant to the volatile growth regulator herbicide, and (ii) an undesired plant which is to be targeted by the volatile growth regulator herbicide and which is sensitive to the volatile growth regulator herbicide; and (c) controlling the undesired plant in the target area with the applied composition; wherein the volatility of the volatile growth regulator herbicide in the target area (e.g., herbicide volatility from plant substrates and/or soil to which herbicide is applied in the target area) is reduced or eliminated relative to a corresponding composition without the monosaccharide applied to the target area. In a refinement, the volatile growth regulator herbicide comprises 2,4-dichlorophenoxyacetic acid (2,4-D) and derivatives thereof. In another refinement, the monosaccharide comprises fructose and optionally glucose. In another refinement, the composition can consist of or consist essentially of (i) water, (ii) one or more volatile growth regulator herbicides (e.g., 0.1 wt. % to 10 wt. %), (iii) one or more monosaccharides (e.g., 0.01 wt. % to 10 wt. %), (iv) optionally one or more non-volatile growth regulator herbicides, and (v) optionally one or more adjuvants (e.g., water conditioners, surfactants, antifoaming agents, anti-drift agents).

In another aspect, the disclosure relates to a composition comprising: (a) water; (b) a volatile growth regulator herbicide; and (c) a monosaccharide; wherein the volatility of the volatile growth regulator herbicide from a target area to which the composition is applied is reduced or eliminated relative to a corresponding composition without the monosaccharide applied to the plant substrate (e.g., reduced herbicide volatility from plant substrates and/or soil to which herbicide is applied in the target area). In a refinement, the volatile growth regulator herbicide and the monosaccharide can be present in the composition at concentrations suitable for application to a target area comprising an undesired plant which is to be targeted by the volatile growth regulator herbicide and which is sensitive to the volatile growth regulator herbicide. In an alternative refinement, the volatile growth regulator herbicide and the monosaccharide can be present in the composition at elevated concentrations unsuitable without prior dilution for application to a target area comprising an undesired plant which is to be targeted by the volatile growth regulator herbicide and which is sensitive to the volatile growth regulator herbicide. In another refinement, the volatile growth regulator herbicide comprises 2,4-dichlorophenoxyacetic acid (2,4-D) and derivatives thereof. In another refinement, the monosaccharide comprises fructose and optionally glucose. In another refinement, the composition can consist of or consist essentially of (a) water, (b) one or more volatile growth regulator herbicides (e.g., 0.1 wt. % to 10 wt. %), (c) one or more monosaccharides (e.g., 0.01 wt. % to 10 wt. %), (d) optionally one or more non-volatile growth regulator herbicides, and (e) optionally one or more adjuvants (e.g., water conditioners, surfactants, antifoaming agents, anti-drift agents).

While the disclosed methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

The disclosure relates to adjuvant- and herbicide-containing compositions (alternatively referenced as herbicide compositions) and related methods for reducing herbicide volatility. The herbicide composition includes a volatile growth regulator herbicide (e.g., 2,4-D and derivatives or analogs thereof) and a monosaccharide adjuvant (e.g., fructose and/or glucose, such as in high-fructose corn syrup). The composition can be applied to a target area to control an (undesired) herbicide-sensitive target plant in the area with the herbicide. The presence of the monosaccharide adjuvant in the composition reduces volatile transport of the herbicide. Reduced volatile transport of the herbicide can reduce damage to other (desired) non-target herbicide-sensitive plants, whether inside or outside of the target area of application.

In one aspect, the disclosure relates to a composition including: (a) water; (b) one or more volatile growth regulator herbicides; and (c) one or more monosaccharides. As noted above, the volatility of the volatile growth regulator herbicide from a target area to which the composition is applied is reduced or eliminated (e.g., reduced herbicide volatility from plant substrates and/or soil to which herbicide is applied in the target area), for example relative to a corresponding composition without the monosaccharide applied to the target area (i.e., an otherwise identical composition but without the monosaccharide). In a refinement, a reduction in volatility can be characterized using the procedure set forth in the examples below (e.g., using wheat and soybean plants or equivalent in a plant growth chamber with a selected herbicide composition including a volatile growth regulator herbicide and a monosaccharide). Suitably, the herbicide composition including the monosaccharide can result in an injury level at 7-DAT, 10-DAT, 14-DAT, and/or 21-DAT which is about 80%, 50% or 30% or less and/or at least about 5%, 10%, 20%, 30%, or 40% of the injury level for the corresponding composition without the monosaccharide.

Volatile growth regulator herbicides often function in a manner similar to plant growth regulators or hormones, and they can operate to induce uncontrolled or unsustainable growth to damage and/or kill plants sensitive to the herbicide. Common volatile growth regulator herbicides include phenoxy herbicides (e.g., organochlorine phenoxy herbicides) such as phenoxy-acetic acids, phenoxy-butyric acids, derivatives thereof, and combinations thereof. A volatile growth regulator herbicide can include a weak acid herbicide or a derivative thereof (e.g., including a weak acid group such as a carboxylic acid group such as an acetic acid or a butyric acid group). The herbicide can be in its acid form, in a derivative form, or in a combination of multiple forms (e.g., multiple forms added to the aqueous herbicide composition or multiple forms resulting from chemical equilibria in aqueous herbicide composition). Example herbicide derivative forms include salts (e.g., metal salt such as alkali and/or alkali earth metal salt; amine salt such as mono-, di-, or tri-alkyl or alkanol amine ($C_1$, $C_2$, $C_3$ or $C_4$ alkyl/alkanol groups such as methyl/methanol, ethyl/ethanol, isopropyl/isopropanol such as in dimethylamine, diethanolamine, isopropylamine, triisopropanolamine salts); organic salt such as choline (e.g., including alkyl, alkanol, and amine/ammonium groups)), esters (e.g., alkyl esters ($C_1$ or $C_3$ to $C_8$ or $C_{12}$ alkyl groups such as isopropyl, ethylhexyl), and amides. As noted, the specific form of the herbicide and its derivatives can relate to the form as supplied to or the form as present in the aqueous herbicide composition resulting from the various equilibrium reactions with the herbicide as supplied, (ionic) species in the water used (e.g., $Ca^{2+}$ and/or $Mg^{2+}$ in hard water), (ionic) species added to the herbicide composition (e.g., water conditioners, surfactants), and pH conditions of the herbicide composition (e.g., commonly pH from 2 to 7.5 or 4.5 to 7.5). Additionally or alternatively, the herbicide can include an aromatic and/or a heteroaromatic group (e.g., benzene- or pyridine-based group as characteristic of common plant hormone-type herbicides, such as the phenoxy family of herbicides, in particular organochlorine phenoxy herbicides).

Examples of suitable volatile growth regulator herbicides include 2,4-dichlorophenoxyacetic acid (2,4-D), 2,4,5-trichlorophenoxyacetic acid (2,4,5-T), 2-methyl-4-chlorophenoxyacetic acid (MCPA), 2-(2-methyl-4-chlorophenoxy) propionic acid (mecoprop, MCPP), 4-(4-chloro-o-tolyloxy) butyric acid (MCPB), 2-(2,4-dichlorophenoxy)propionic acid (dichlorprop, 2,4-DP), (2,4-dichlorophenoxy)butyric acid (2,4-DB), 3,6-dichloro-2-methoxybenzoic acid (dicamba), 4-amino-3,5,6-trichloropicolinic acid (picloram), 3,5,6-trichloro-2-pyridinyloxyacetic acid (triclopyr), 3,6-dichloro-2-pyridinecarboxylic acid (clopyralid), derivatives thereof, and combinations thereof. In some embodiments, the herbicide composition can include more than one type of volatile growth regulator herbicide (e.g., two, three, or four different types of volatile growth regulator herbicides in admixture). In other embodiments, the herbicide composition includes only one type of volatile growth regulator herbicide (e.g., a single type but possibly including one or more of an acid, salt, and ester form of the herbicide type). In a particular embodiment, 2,4-D and derivatives thereof are the only volatile growth regulator herbicides in the herbicide composition.

The volatility of the volatile growth regulator herbicide can be characterized in terms of its vapor pressure in the aqueous herbicide composition (e.g., in the form as present in the composition, if different from the form as added the composition). The vapor pressure of the herbicide can be at least $1 \times 10^{-6}$ Pa, $1 \times 10^{-5}$ Pa, $1.3 \times 10^{-5}$ Pa, $1.5 \times 10^{-5}$ Pa, $1.8 \times 10^{-5}$ Pa, $1 \times 10^{-4}$ Pa, or $1 \times 10^{-3}$ Pa and/or up to $1 \times 10^{-4}$ Pa, $1 \times 10^{-3}$ Pa, $1 \times 10^{-2}$ Pa, $1 \times 10^{-1}$ Pa, $1 \times 10^{0}$ Pa, or $1 \times 10^{1}$ Pa. By way of illustration, approximate vapor pressures of common forms of 2,4-D include $1.9 \times 10^{-5}$ Pa (acid), $1.3 \times 10^{-5}$ Pa (dimethylamine salt), $3.2 \times 10^{-4}$ Pa (butoxyethyl ester), $4.8 \times 10^{-4}$ Pa (2-ethylhexyl ester), and $1.9 \times 10^{1}$ Pa (isopropyl ester). Other common forms of 2,4-D that can form the corresponding volatile acid in an aqueous solution include metal salts (e.g., alkali and alkali metal salts such as the sodium salt), the isopropylamine salt, and the triisopropanolamine salt.

The specific amount of the volatile growth regulator herbicide in the herbicide composition is not particularly limited, for example generally being guided by herbicide manufacturer-recommended application rates and the intended target plant. Suitably, the herbicide is present in the composition in an amount ranging from 0.01 wt. % to 10 wt. % (e.g., 0.1 wt. % to 5 wt. %). In various embodiments, the herbicide is present in an amount of at least about 0.01 wt. %, 0.1 wt. %, 0.2 wt. %, 0.5 wt. %, 0.7 wt. %, or 1 wt. % and/or up to about 1.5 wt. %, 2 wt. %, 3 wt. %, 5 wt. % or 10 wt. % relative the composition as a whole. The foregoing amounts can apply to herbicide species individually or all herbicide species collectively present (e.g., multiple forms of the same type of herbicide and/or multiple types of different herbicides).

In some embodiments, the herbicide composition includes an additional herbicide which is not a volatile growth regulator herbicide. For example, the composition can include one or more non-volatile growth regulator herbicides (e.g., non-volatile herbicides and/or non-growth regulator herbicides) such as those disclosed in U.S. Pat. No. 5,945,377, incorporated herein by reference in its entirety. In an embodiment, the additional herbicide can include an amino acid derivative herbicide, for example a glyphosate herbicide (e.g., N-(phosphonomethyl)glycine (glyphosate)

including various salts and other derivatives thereof). Alternatively, the herbicide composition can be free of non-volatile growth regulator herbicides.

The monosaccharide suitably includes one or more of fructose, glucose, and mannose, in particular including fructose alone or in combination with glucose. In some embodiments, fructose or fructose and glucose is/are the only monosaccharide(s) (or saccharide(s) more generally) in the composition (e.g., the composition is free from other (added) monosaccharides or saccharides more generally). Alternatively or additionally, the monosaccharide can include a corn syrup product such as high-fructose corn syrup. High-fructose corn syrup (HFCS) suitably includes at least 40 wt. %, 50 wt. %, or 60 wt. % and/or up to 50 wt. %, 60 wt. %, 70 wt. % or 90 wt. % fructose relative to total monosaccharides (e.g., balance glucose) in the syrup. Examples include HFCS 42/58, 55/45, or 90/10 or blends thereof (e.g., about 20 wt. %, 25 wt. %, or 30 wt. % water with the substantial balance being a combination of fructose and glucose in the indicated w/w ratio). For example, the ratio of fructose/glucose (w/w) can be 40/60 to 45/55, 40/60 to 60/40, 50/50 to 60/40, 40/60 to 90/10, about 42/58, about 55/45, or about 90/10. In some embodiments, where the high-fructose corn syrup is the only source of monosaccharides or saccharides in the herbicide composition. In other embodiments, the herbicide composition is free or substantially free from saccharides other than the monosaccharide (e.g., free from disaccharides such as sucrose, free from other oligosaccharides (such as 3-10 saccharide units), free from other polysaccharides (such as more than 10 saccharide units), such as having no added saccharides of the indicated type).

The specific amount of the monosaccharide in the herbicide composition is not particularly limited. Suitably, the monosaccharide is present in the composition in an amount ranging from 0.1 wt. % to 10 wt. % (e.g., 0.5 wt. % to 5 wt. % or 0.7 wt. % to 3 wt. %). In various embodiments, the monosaccharide is present in an amount of at least about 0.1 wt. %, 0.2 wt. %, 0.5 wt. %, 0.7 wt. %, or 1 wt. % and/or up to about 1.5 wt. %, 2 wt. %, 3 wt. %, 5 wt. % or 10 wt. % relative the composition as a whole. The foregoing amounts can apply to monosaccharide species individually or all monosaccharide species collectively present (e.g., fructose and glucose combined).

The herbicide composition additional can contain one or more additives or adjuvants known in the art and at commonly employed levels for the same. For example, the composition can include one or more water conditioners (e.g., ammonium sulfate and/or ammonium nitrate for hard water management), one or more surfactants (e.g., nonionic, anionic, cationic), one or more antifoaming agents (e.g., siloxanes such as polydimethylsiloxane), one or more anti-drift agents (e.g., polyvinyl polymers such as polyacylamide), etc. The additives can be included in any suitable amount, for example in an amount ranging from 0.01 wt. % to 10 wt. % (e.g., 0.1 wt. % to 5 wt. %).

The disclosure also relates to a method for reducing volatile transport of volatile herbicides. The method includes: (a) providing the herbicide composition according to any of it various embodiments and refinements; (b) applying the composition to a target area including: (i) (optionally) a first desired plant which is resistant or tolerant to the volatile growth regulator herbicide, and (ii) an undesired plant (e.g., a post-emergent undesired plant) which is to be targeted by the volatile growth regulator herbicide and which is sensitive to the volatile growth regulator herbicide; and (c) controlling the undesired plant in the target area with the applied composition. The volatility of the volatile growth regulator herbicide in the target area (e.g., herbicide volatility from plant substrates and/or soil to which herbicide is applied in the target area) is reduced or eliminated relative to a corresponding composition without the monosaccharide applied to the target area. As described above relative the composition, the reduction in volatility can be characterized using the procedure set forth in the examples below (e.g., using wheat and soybean plants or equivalent in a plant growth chamber with a selected herbicide composition including a volatile growth regulator herbicide and a monosaccharide).

The herbicide composition is often provided as a concentrate which is diluted with water (usually hard water) in the field prior to application to a target area. The diluted composition provides sufficient volatile growth regulator herbicide to kill or otherwise control the undesired plants in the target area. The application rate of the herbicide can vary as appropriate for a particular herbicide and a particular target plant, but common rates range from about 0.01 kg a.i./ha to 4.0 kg a.i./ha, commonly applied (e.g., sprayed with a sprayer) at rates of about 40 L/ha to 300 L/ha of the dilute composition, with some undesired plants requiring more herbicide than others.

The undesired plant in the target area is not particularly limited and can include any plant which is sensitive to the volatile growth regulator herbicide and which is desired to be killed, damaged, or otherwise controlled by the application of the herbicide. Sensitive plants generally include any plants susceptible to being killed, damaged, or otherwise controlled by the herbicide, regardless of whether the plants are natural varieties (e.g., naturally occurring wild type varieties, varieties bred for a particular trait) or genetically modified varieties to incorporate (heterologous) genetic traits related to something other than resistance to the herbicide. The undesired plant suitably can include one or more types of broadleaf weeds in the target area. Example broadleaf weeds include marestail, velvetleaf, and common lambsquarters. These examples are illustrative and the herbicide composition more generally can be used to control any undesired herbicide-sensitive plant.

In some embodiments, the target area also includes planted therein one or more first desired plants which are resistant or tolerant to the volatile growth regulator herbicide. The first desired plant can represent a crop plant or other valuable plant in a field or other cultivated area where it is desired to eliminate of the undesired plant (e.g., where the undesired plant has an adverse effect on the first desired plants and/or the undesired plant is aesthetically displeasing). In this case, the herbicide composition can be applied to the target area to control the undesired plant without substantially adversely affecting the first desired plant (e.g., due to its resistance or tolerance to the volatile growth regulator herbicide). Resistant or tolerant plants include those plants which are generally not susceptible to control by the volatile growth regulator herbicide, for example as a result of one or more naturally occurring resistance or tolerance traits (e.g., traits in naturally occurring wild type varieties or natural varieties bred for a particular trait, whether or not related to herbicide resistance) and/or one or more (heterologous) genetic traits conferring herbicide resistance in a genetically modified plant. Examples of resistant or tolerant plants (e.g., as the first plant) include resistant cash crops (e.g., resistant soybean, resistant corn, resistant canola, resistant cotton, resistant wheat; whether or not resistance results from a genetically modified trait, natural trait, or bred trait), tolerant cash crops (e.g., wheat;

whether or not tolerance results from a genetically modified trait, natural trait, or bred trait), grasses such as turfgrasses (e.g., whether or not tolerance or resistance results from a genetically modified trait, natural trait, or bred trait). These examples are illustrative and the target area more generally can include any desired herbicide-resistant or herbicide-tolerant plants.

In an embodiment, the target area is adjacent to a collateral area includes planted therein one or more second desired plants which are to be protected from the volatile growth regulator herbicide and which are sensitive to the volatile growth regulator herbicide. The second desired plant can represent a crop plant or other valuable plant in a field or other cultivated area which is adjacent to the target area where it is desired to eliminate the undesired plant. The proximity between the target area and the collateral area is not particularly limited. In some cases, the target area and the collateral area can be about 1 m or less, 10 m or less, 100 m or less, 1 km or less, or 10 km or less from each other, for example within about 1 m to 10 m, 10 m to 100 m, 100 m to 1 km, or 1 km to 10 km of each other (e.g., within about 1 m, 10 m, 100 m, 1 km, or 10 km of each other). Because the volatility of the volatile growth regulator herbicide as applied to the target area is reduced or eliminated, damage to the second desired plant in the collateral area is similarly reduced or eliminated based on a suppression of volatile transport of the herbicide to the collateral area. For example, damage to the second desired plant is reduced relative that which would otherwise be observed resulting from to a corresponding herbicide composition without the monosaccharide applied to the target area (e.g., not more than 50%, 20%, 10%, 5%, 2% or 1% damage relative to the corresponding control herbicide composition; in cases where some minor volatilization can still occur, the relative damage could be at least 0.5%, 1%, 2%, 5% or 10% and less than one of the previous upper bounds). Sensitive second desired plants in the collateral area generally include cash crops, ornamental plants, and wild plant life (e.g., varieties without any natural, bred, or transgenically introduced resistance or tolerance). Examples of sensitive second desired plants include soybean plants, corn plants, sugar beet plants, tomato plants, cucumber plants, grape plants, cotton plants, melon plants, dry bean plants, potato plants, fruit plants (e.g., trees or bushes such as for cherry trees, apple trees, orange trees), and ornamental plants (e.g., flowers or otherwise). These examples are illustrative and the collateral area more generally can include any desired herbicide-sensitive plants.

The specific manner in which the undesired plant in the target area is controlled by the herbicide is not particularly limited. Control of the undesired plant generally corresponds to the intended herbicidal activity for the undesired plant, for example one or more of killing and/or damaging of the undesired plant, preventing further reproduction and/or growth of the undesired plant, etc. Conversely, the herbicide-sensitive desired plants, when present in the target or adjacent collateral areas, respectively, suitably are not substantially adversely affected or otherwise controlled by the herbicide (e.g., killed, damaged or injured) due to a reduction in or elimination of volatile transport of the herbicide from its area or substrate of application.

EXAMPLES

The following examples illustrate the disclosed compositions and methods, but are not intended to limit the scope of any claims thereto.

Volatilization of herbicides from soils and plants can result in undesirable loss of the active herbicide ingredient as well as unintended injury to nearby plants. These examples illustrate herbicide compositions and methods according to the disclosure including herbicide composition adjuvants to reduce or eliminate herbicide volatility from an area to which the herbicide composition is applied (e.g., volatile loss and transport of the herbicide component of the composition away from an applied plant substrate and/or from an applied soil or ground surface).

A wide range of soil, plant, environmental, and herbicide factors (e.g., vapor pressure and water solubility of herbicide, surface characteristics) can affect herbicide volatility from soils and plants. Comparison of the volatilization would be most readily visualized by appropriate bioassay systems. These examples illustrate a bioassay system for evaluating herbicide volatilization from plant substrates. In the bioassay system, a herbicide composition including a volatile growth regulator herbicide (2,4-D) and one or more adjuvants was applied foliarly to wheat plants (amber red wheat). Twenty minutes later, soybean plants (PIONEER 92M92 soybean plants) sensitive to the volatile growth regulator herbicide were placed in the middle of the sprayed wheat plants. Visual evaluation of the soybean plants 1 to 3 weeks later showed differences in plant injury resulting from the applied herbicide composition and the volatility of the herbicide component thereof.

Measurement of herbicide volatility from wheat to soybean. Plant growth chambers formed from clear circular plastic containers (about 27 cm diameter) with a spacer pot in the middle were used to grow wheat plants (from amber red wheat seed) in a professional potting mix. The wheat plants were sprayed with various herbicide compositions including the dimethylamine (DMA) salt of 2,4-D (2,4-D-DMA) or 2,4-D in acid form (2,4-D acid). The herbicide compositions were prepared and applied at a rate of 0.84 kg a.i./ha (active ingredient per hectare) at 93.5 L/ha (10 gal/acre) and 172 kPa (25 psi) using a flat fan nozzle tip (TEEJET XR8001E or equivalent; available from Spraying Systems, Co., Wheaton, Ill.). As indicated in Table 1 below, the herbicide compositions additionally included one or more adjuvants (expressed as wt. % relative to the herbicide composition) for application with the herbicide.

Soybean plants (PIONEER 92M92) were seeded into 10 cm diameter round pots. A single pot with soybean plants was placed in the center of each circular plastic container 20 minutes after spraying the wheat with the respective herbicide treatment composition (i.e., with the soybean plant pot replacing the spacer pot present during wheat growth and herbicide composition application). Open clear plastic cylinders were then taped to the top of the circular containers and placed in a greenhouse. The open clear plastic cylinders were tall enough to add an open circumferential wall (about 28 cm high and having a circular top opening about 20 cm in diameter) to the plant growth chambers (i.e., with the height being relative to the soil surface for the wheat and soybean plants). Visual evaluation of soybean injury was evaluated 7, 10, 14, and 21 days after treatment/application (DAT) of the herbicide composition and continued growth under greenhouse conditions. Data were subjected to analysis of variance using PROC GLM in SAS and the results are the means of two experiments with four replications in each.

Results. The plant growth chambers described above effectively contained the vapors of the volatile herbicides so that plants in adjacent growth chambers were not affected by the particular herbicide composition applied to a particular chamber. As shown in Table 1 below, injury symptoms on the sensitive soybean plants were observed from 2,4-D volatility.

colamine salt and dimethylamine salt, respectively), 14-DAT (about 31% and 39% injury) and 21-DAT (about 41% and 41% injury).

TABLE 1

Volatile Herbicide Injury to Soybean Plants

| Ex. | Herbicide | Adjuvant | % Injury (7-DAT) | % Injury (10-DAT) | % Injury (14-DAT) | % Injury (21-DAT) |
|---|---|---|---|---|---|---|
| 1 | None (tap water control) | None | 0 H | 0 G | 0 I | 0 G |
| 2 | 2,4-D DMA | None | 19 ABC | 27 AB | 28 CDEF | 26 ABCD |
| 3 | 2,4-D DMA | 0.5% G, 0.5% H | 23 A | 25 BC | 29 BCDE | 25 ABCD |
| 4 | 2,4-D DMA | 1% G | 13 CDEF | 23 BCD | 30 ABCD | 21 CDE |
| 5 | 2,4-D DMA | 1% R | 11 EFG | 12 EF | 19 DEFGH | 6 EFG |
| 6 | 2,4-D DMA | 1% R + 1% H | 10 EFG | 9 F | 15 GH | 10 DEFG |
| 7 | 2,4-D DMA | 1% H | 6 FGH | 16 DEF | 20 DEFGH | 9 DEFG |
| 8 | 2,4-D DMA | 1% N | 17 ABCDE | 26 ABC | 25 CDEFG | 19 DEF |
| 9 | 2,4-D DMA | 0.3% S | 21 AB | 33 A | 31 ABCD | 24 ABCD |
| 10 | 2,4-D DMA | 0.3% S + 1% H | 23 A | 25 BC | 28 CDEF | 23 BCDE |
| 11 | 2,4-D DMA | 2.3% SH | 3 H | 18 CDE | 18 EFGH | 19 DEF |
| 12 | 2,4-D DMA | 1.3% M | 11 DEFG | 30 AB | 32 ABC | 24 ABCD |
| 13 | 2,4-D Acid | 0.5% T | 11 EFG | 23 BCD | 25 CDEFG | 24 ABCD |
| 14 | 2,4-D Acid | 0.5% T + 0.5% H | 19 ABC | 24 BCD | 24 CDEFG | 18 DEF |
| 15 | 2,4-D DMA | 0.5% T | 11 DEFG | 30 AB | 41 A | 40 A |
| 16 | 2,4-D DMA | 1.5% CJ | 23 A | 29 AB | 35 ABC | 36 ABC |
| 17 | 2,4-D DMA | 2% A | 18 ABCD | 24 BC | 31 ABCD | 24 ABCD |
| 18 | 2,4-D DMA | 2.5% C | 16 ABCDE | 24 BCD | 28 CDEF | 20 CDEF |
| 19 | 2,4-D DMA | 1.25% C + 1% H | 5 GH | 0 G | 14 GH | 0 G |
| | | LSD (0.05): | 7 | 8 | 12 | 17 |

Abbreviations:
A: Ammonium sulfate (AMS)
C: CLASS ACT NG adjuvant (ammonium sulfate water conditioner, non-ionic surfactant, corn syrup, and antifoaming agent; available from AgriSolutions, Brighton, IL)
CJ: Cranberry juice (100%)
G: Glycerin
H: High fructose corn syrup 55/45
LSD (0.05): least significant difference at 95% confidence (like letters indicate no statistical difference)
M: Molasses
N: NTANK adjuvant (including monocarbamide dihydrogen sulfate, amine phosphates; available from Adjuvants Plus, Kingsville, ON)
R: REDDY IT adjuvant (polyethoxylated phosphate esters, polyethoxylated amines, and methylated seed oils; available from Adjuvants Plus, Kingsville, ON)
S: SYLGARD 309 adjuvant (non-ionic silicone surfactant; available from Dow Corning, Midland, MI)
SH: SUPERB HC adjuvant (phytobland paraffinic oil, high fructose corn syrup, polyoxyethylene sorbitan fatty esters, petroleum distillates, and surfactants; available from AgriSolutions, Brighton, IL)
T: Tallow amine (polyethoxylated tallow amine surfactant)

As shown in Table 1, soybean plant injury resulting from herbicide volatility was substantially reduced with the inclusion of a monosaccharide adjuvant such as high-fructose corn syrup (HFCS), both relative to herbicide compositions without adjuvants and herbicide compositions with other adjuvants. The HFCS includes about 24 wt. % water and 76 wt. % monosaccharides (55 wt. % fructose and 45 wt. % glucose relative to total monosaccharides). For instance, the injury levels for Example 7 (2,4-D-DMA with 1% HFCS) were about 32%, 59%, 71%, and 35% of the injury levels for Example 2 (2,4-D-DMA without adjuvant) at 7-DAT, 10-DAT, 14-DAT, and 21-DAT, respectively. Herbicide compositions with a molasses adjuvant (including about 20 wt. % water, about 13 wt. % fructose, about 12 wt. % glucose, about 30 wt. % sucrose, and about 20 wt. % higher saccharides such as dextrose), in contrast, exhibited plant injury which was the same or worse than control herbicide compositions with no adjuvant.

Similar trials were also performed using herbicide compositions with volatile dicamba volatile growth regulator herbicides (dimethylamine salt of dicamba (BANVEL) and diglycolamine salt of dicamba (CLARITY)) at 1.12 kg a.i./ha in place of 2,4-D and without any adjuvants. Similar to the control Example 2 in Table 1 above, injury symptoms on the sensitive soybean plants were observed from dicamba volatility at 7-DAT (about 28% and 39% injury for digly- Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method for reducing volatile transport of volatile herbicides, the method comprising:
    (a) providing a composition comprising: (i) water, (ii) a volatile growth regulator herbicide, and (iii) a monosaccharide, wherein:
        the volatile growth regulator herbicide comprises a 2,4-D herbicide selected from the croup consisting of 2,4-dichlorophenoxyacetic acid (2,4-D), alkali metal salts thereof, alkali earth metal salts thereof, $C_1$-$C_4$ mono-, di-, tri-alkylamine salts thereof, $C_1$-$C_4$ mono-, di-, tri-alkanolamine salts thereof, choline salts thereof, $C_1$-$C_{12}$ alkyl esters thereof, and combinations thereof, and
        the monosaccharide is selected from the group consisting of fructose, glucose, mannose, and combinations thereof, wherein the monosaccharide is present in the composition in an amount ranging from 0.5 wt. % to 10 wt. %;
    (b) applying the composition to a target area comprising: (i) optionally a first desired plant which is resistant or tolerant to the volatile growth regulator herbicide, and (ii) an undesired plant which is to be targeted by the volatile growth regulator herbicide and which is sensitive to the volatile growth regulator herbicide, wherein the target area is adjacent to a collateral area comprising a second desired plant which is to be protected from the volatile growth regulator herbicide and which is susceptible to being one or more of killed and damaged by the volatile growth regulator herbicide; and
    (c) controlling the undesired plant in the target area with the applied composition, wherein controlling the undesired plant comprises one or more of killing the undesired plant and damaging the undesired plant;
    wherein:
        the volatility of the 2,4-D herbicide in the target area is reduced or eliminated relative to a corresponding composition without the monosaccharide applied to the target area; and
        damage to the second desired plant in the collateral area is reduced or eliminated relative to a corresponding composition without the monosaccharide applied to the target area.

2. The method of claim 1, wherein the volatile growth regulator herbicide comprises at least one of an aromatic and a heteroaromatic group.

3. The method of claim 1, wherein the composition comprises two or more types of volatile growth regulator herbicides in admixture.

4. The method of claim 1, wherein the volatile growth regulator herbicide has a vapor pressure of at least $1 \times 10^{-6}$ Pa.

5. The method of claim 1, wherein the volatile growth regulator herbicide is present in the composition in an amount ranging from 0.01 wt. % to 10 wt. %.

6. The method of claim 1, wherein the monosaccharide comprises fructose.

7. The method of claim 1, wherein the monosaccharide comprises high-fructose corn syrup.

8. The method of claim 1, wherein the composition has no added saccharides other than fructose, glucose, and mannose.

9. The method of claim 1, wherein the monosaccharide is present in the composition in an amount ranging from 0.1 wt. % to 10 wt. %.

10. The method of claim 1, wherein the composition further comprises an additional herbicide which is not a volatile growth regulator herbicide.

11. The method of claim 1, wherein the composition further comprises at least one of ammonium sulfate, ammonium nitrate, and a surfactant.

12. The method of claim 1, wherein the target area comprises the first desired plant which is resistant or tolerant to the volatile growth regulator herbicide.

13. The method of claim 1, wherein the undesired plant to be targeted comprises one or more broadleaf weeds.

14. The method of claim 1, wherein the composition is free from glyphosate herbicides.

15. The method of claim 1, wherein the volatile growth regulator herbicide further comprises one or more of 3,6-dichloro-2-methoxybenzoic acid (dicamba), alkali metal salts thereof, alkali earth metal salts thereof, $C_1$-$C_4$ mono-, di-, tri-alkylamine salts thereof, $C_1$-$C_4$ mono-, di-, tri-alkanolamine salts thereof, choline salts thereof, and $C_1$-$C_{12}$ alkyl esters thereof.

16. The method of claim 1, wherein the composition further comprises a glyphosate herbicide.

17. The method of claim 1, wherein the composition further comprises glycerin.

18. The method of claim 1, wherein
    the volatile growth regulator herbicide comprises a $C_1$-$C_4$ alkylamine salt of dichlorophenoxyacetic acid (2,4-D);
    the monosaccharide is a combination of fructose and glucose in the form of high-fructose corn syrup; and
    the monosaccharide is present in the composition in an amount ranging from 0.5 wt. % to 3 wt. %.

19. The method of claim 1, wherein
    the volatile growth regulator herbicide comprises a $C_2$-$C_4$ alkylamine salt of dichlorophenoxyacetic acid (2,4-D);
    the monosaccharide is a combination of fructose and glucose; and
    the monosaccharide is present in the composition in an amount ranging from 0.5 wt. % to 3 wt. %.

20. The method of claim 1, wherein:
    the target area is a first crop field, the first desired plant is present therein, and the first desired plant is a first crop plant; and
    the collateral area is a second crop field separate from the first crop field, and the second desired plant is a second crop plant.

21. The method of claim 20, wherein the first crop field and the second crop field are separated by a distance in a range from 100 m to 10 km.

22. The method of claim 1, wherein the target area and the collateral area are separate areas separated by a distance in a range from 10 m to 1 km.

* * * * *